US007923464B2

(12) United States Patent
Larsen et al.

(10) Patent No.: US 7,923,464 B2
(45) Date of Patent: Apr. 12, 2011

(54) BENZIMIDAZOLE DERIVATIVES AND THEIR USE FOR MODULATING THE GABA$_A$ RECEPTOR COMPLEX

(75) Inventors: Janus S. Larsen, Holbæk (DK); Lene Teuber, Værløse (DK); Philip K. Ahring, Bagsværd (DK); Elsebet Østergaard Nielsen, København K (DK); Naheed Mirza, Birkerød (DK)

(73) Assignee: Neurosearch A/S, Ballerup (DK)

( * ) Notice: Subject to any disclaimer, the term of this patent is extended or adjusted under 35 U.S.C. 154(b) by 418 days.

(21) Appl. No.: 12/085,769

(22) PCT Filed: Dec. 4, 2006

(86) PCT No.: PCT/EP2006/069237
§ 371 (c)(1),
(2), (4) Date: May 30, 2008

(87) PCT Pub. No.: WO2007/065864
PCT Pub. Date: Jun. 14, 2007

(65) Prior Publication Data
US 2009/0048321 A1    Feb. 19, 2009

Related U.S. Application Data

(60) Provisional application No. 60/742,535, filed on Dec. 6, 2005, provisional application No. 60/851,291, filed on Oct. 13, 2006.

(30) Foreign Application Priority Data

Dec. 5, 2005   (DK) .................................. 2005 01719
Oct. 12, 2006  (DK) .................................. 2006 01326

(51) Int. Cl.
*A61K 31/4184*    (2006.01)
*C07D 235/04*     (2006.01)

(52) U.S. Cl. .................. 514/394; 548/302.7; 548/304.4; 514/385; 514/393

(58) Field of Classification Search ............... 548/302.7, 548/304.4; 514/385, 393, 394
See application file for complete search history.

(56) References Cited

U.S. PATENT DOCUMENTS

| 5,360,809 | A   | 11/1994 | Axelsson et al.          |
|-----------|-----|---------|--------------------------|
| 6,218,547 | B1  | 4/2001  | Teuber et al.            |
| 6,503,925 | B1  | 1/2003  | Teuber et al.            |
| 6,649,609 | B2  | 11/2003 | Teuber et al.            |
| 6,710,044 | B2  | 3/2004  | Teuber et al.            |
| 6,936,613 | B2  | 8/2005  | Teuber et al.            |
| 7,335,777 | B2* | 2/2008  | Teuber et al. .............. 548/304.7 |
| 7,419,995 | B2  | 9/2008  | Crew et al.              |
| 7,521,448 | B2  | 4/2009  | Bolger et al.            |
| 7,700,638 | B2* | 4/2010  | Hamilton et al. ............ 514/394 |
| 7,776,900 | B2* | 8/2010  | Teuber et al. ................. 514/394 |
| 2003/0055055 | A1 | 3/2003 | Teuber et al.            |

FOREIGN PATENT DOCUMENTS

| WO | WO 96/33194 A1   | 10/1996 |
|----|------------------|---------|
| WO | WO 99/19323 A1   | 4/1999  |
| WO | WO 02/50057 A1   | 6/2002  |
| WO | WO 2004/087137 A1 | 10/2004 |
| WO | WO 2004/087690 A2 | 10/2004 |
| WO | WO 2005/040131 A1 | 5/2005  |
| WO | WO-2006/060381 A  | 6/2006  |
| WO | WO-2006/108800 A  | 10/2006 |
| WO | WO-2007/110374 A1 | 10/2007 |

OTHER PUBLICATIONS

International Search Report for International Application No. PCT/EP2006/061417 mailed Jul. 28, 2006.
Non-Final Office Action for U.S. Appl. No. 11/887,780 mailed Mar. 10, 2010.
Restriction Requirement for U.S. Appl. No. 11/887,780 mailed Dec. 17, 2009.

* cited by examiner

*Primary Examiner* — Golam M Shameem
(74) *Attorney, Agent, or Firm* — Birch, Stewart, Kolasch & Birch, LLP.

(57) ABSTRACT

This invention relates to novel benzimidazole derivatives, pharmaceutical compositions containing these compounds, and methods of treatment therewith.
The compounds of the invention are useful in the treatment of central nervous system diseases and disorders, which are responsive to modulation of the GABA$_A$ receptor complex, and in particular for combating anxiety and related diseases.

8 Claims, No Drawings

BENZIMIDAZOLE DERIVATIVES AND THEIR USE FOR MODULATING THE GABA$_A$ RECEPTOR COMPLEX

This application is the National Phase of PCT/EP2006/069237 filed on Dec. 4, 2006, which claims priority under 35 U.S.C. 119(e) to U.S. Provisional Application Nos. 60/742,535 and 60/851,291 filed on Dec. 6, 2005 and Oct. 13, 2006; respectively and under 35 U.S.C. 119(a) to Patent Application No. PA 2005 01719 and PA 2006 01326 filed in Denmark on Dec. 5, 2005 and Oct. 12, 2006; respectively. All of these prior applications are hereby expressly incorporated by reference into the present application.

TECHNICAL FIELD

This invention relates to novel benzimidazole derivatives, pharmaceutical compositions containing these compounds, and methods of treatment therewith.

The compounds of the invention are useful in the treatment of central nervous system diseases and disorders, which are responsive to modulation of the GABA$_A$ receptor complex, and in particular for combating anxiety and related diseases.

BACKGROUND ART

The modulatory sites on the GABA$_A$ receptor complex, such as for example the benzodiazepine binding site, are the target for anxiolytic drugs, such as the classical anxiolytic benzodiazepines. However, they are associated with a number of undesirable features.

Multiple isoforms of the GABA$_A$ receptor exist; each receptor is a pentameric complex comprising subunits drawn from $\alpha_{1-6}$, $\beta_{1-3}$, $\gamma_{1-3}$, $\delta$, $\epsilon$, and $\theta$ subunit isoforms. The classical anxiolytic benzodiazepines show no subtype selectivity. It has been suggested that one of the key elements in the disadvantages of the classical benzodiazepanes (such as sedation, dependency, and cognitive impairment) is relates to the $\alpha$1 subunit of the GABA$_A$ receptors. Thus compounds with selectivity for the $\alpha$2 and/or $\alpha$3 subunits over the $\alpha$1 subunit are expected to have an improved side effect profile.

Thus, there is still a strong need for compounds with an optimised pharmacological profile. Furthermore, there is a strong need to find effective compounds without unwanted side effects associated with older compounds.

SUMMARY OF THE INVENTION

In its first aspect, the invention provides a compound of Formula I:

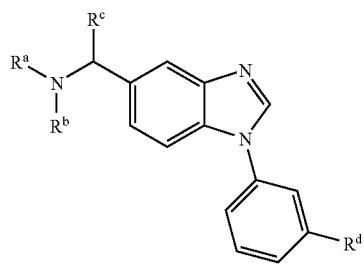

(I)

or an N-oxide thereof, any of its isomers or any mixture of its isomers, or a pharmaceutically acceptable salt thereof, wherein $R^a$, $R^b$, $R^c$ and $R^d$ are defined as below.

In its second aspect, the invention provides a pharmaceutical composition, comprising a therapeutically effective amount of a compound of the invention, or an N-oxide thereof, any of its isomers or any mixture of its isomers, or a pharmaceutically acceptable salt thereof, together with at least one pharmaceutically acceptable carrier, excipient or diluent.

In a further aspect, the invention provides the use of a compound of the invention, or an N-oxide thereof, any of its isomers or any mixture of its isomers, or a pharmaceutically acceptable salt thereof, for the manufacture of a pharmaceutical composition for the treatment, prevention or alleviation of a disease or a disorder or a condition of a mammal, including a human, which disease, disorder or condition is responsive to modulation of the GABA$_A$ receptor complex in the central nervous system.

In a still further aspect, the invention relates to a method for treatment, prevention or alleviation of a disease or a disorder or a condition of a living animal body, including a human, which disorder, disease or condition is responsive to modulation of the GABA$_A$ receptor complex in the central nervous system, which method comprises the step of administering to such a living animal body in need thereof a therapeutically effective amount of a compound of the invention, or an N-oxide thereof, any of its isomers or any mixture of its isomers, or a pharmaceutically acceptable salt thereof.

Other objects of the invention will be apparent to the person skilled in the art from the following detailed description and examples.

DETAILED DISCLOSURE OF THE INVENTION

Substituted Benzimidazole Derivatives

In its first aspect the present invention provides a compound of the general Formula (I):

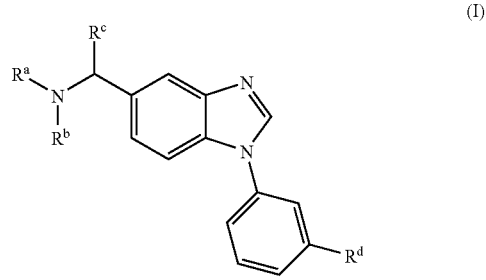

(I)

or an N-oxide thereof, any of its isomers or any mixture of its isomers, or a pharmaceutically acceptable salt thereof, wherein $R^a$, $R^b$ and $R^c$ independent of each other represent hydrogen, alkyl, cycloalkyl, cycloalkylakyl, alkenyl, alkynyl, hydroxy, alkoxy, alkoxyalkyl, formyl, alkylcarbonyl or alkoxyalkylcarbonyl;

$R^d$ represents an aryl group;

which aryl group is optionally substituted with one or more substituents independently selected from the group consisting of:

halo, hydroxy, R'R"N—, R'R"N-alkyl, R'—SO$_2$—N(R")—, R'-(C=O)—, R'R"N—(C=O)—, cyano, nitro, trifluoromethyl, trifluoromethoxy, alkoxy, cycloalkoxy, alkyl, cycloalkyl, cycloalkylalkyl, methylenedioxy, ethylenedioxy, alkenyl, alkynyl and —(CR'R")$_n$—R$^e$;
wherein R' and R" independent of each other are hydrogen or alkyl;
n is 0 or 1; and
R$^e$ represents a heterocyclic ring,
which heterocyclic ring may optionally be substituted with: halo, trifluoromethyl, trifluoromethoxy, cyano, nitro, alkyl, hydroxyl or alkoxy.

In one embodiment, R$^a$ represents hydrogen or alkyl. In a special embodiment, R$^a$ represents hydrogen.

In a further embodiment, R$^b$ represents hydrogen, alkyl, formyl or alkylcarbonyl. In a special embodiment, R$^b$ represents hydrogen. In a further embodiment, R$^b$ represents formyl. In a still further embodiment, R$^b$ represents alkylcarbonyl, such as acetyl.

In a still further embodiment, R$^c$ represents hydrogen or alkyl. In a special embodiment, R$^c$ represents alkyl, such as methyl.

In a special embodiment, R$^a$ represents hydrogen, R$^b$ represents hydrogen and R$^c$ represents methyl. In a further embodiment, R$^a$ represents hydrogen, R$^b$ represents formyl and R$^c$ represents methyl. In a still further embodiment, R$^a$ represents hydrogen, R$^b$ represents acetyl and R$^c$ represents methyl.

In a further embodiment, R$^d$ represents an aryl group; which aryl group is optionally substituted with one or more substituents independently selected from the group consisting of: halo, hydroxy, R'R"N—, R'R"N-alkyl, cyano, nitro, trifluoromethyl, trifluoromethoxy, alkoxy, cycloalkoxy, alkyl, cycloalkyl, cycloalkylalkyl, alkenyl, and alkynyl; wherein R' and R" independent of each other are hydrogen or alkyl.

In a further embodiment, R$^d$ represents optionally substituted phenyl.

In a still further embodiment, R$^d$ represents

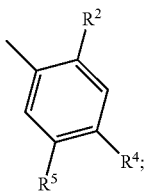

wherein R$^2$, R$^4$ and R$^5$ independent of each other represent hydrogen, halo, cyano, trifluoromethyl, trifluoromethoxy, alkyl or alkoxy.

In one embodiment, R$^2$, R$^4$ and R$^5$ each represent hydrogen.

In a further embodiment, R$^2$ represents halo, cyano, trifluoromethoxy or alkoxy; R$^4$ represents hydrogen; and R$^5$ represents hydrogen. In a special embodiment, R$^2$ represents halo, such as fluoro. In a further embodiment, R$^2$ represents cyano. In a still further embodiment, R$^2$ represents trifluoromethoxy. In a further embodiment, R$^2$ represents alkoxy, such as methoxy.

In a still further embodiment, R$^4$ represents halo, such as fluoro; R$^2$ represents hydrogen; and R$^5$ represent hydrogen.

In a further embodiment, R$^2$ represents alkoxy, such as methoxy; R$^4$ represents hydrogen; and R$^5$ represent halo, such as fluoro or chloro.

In a still further embodiment, R$^d$ represents

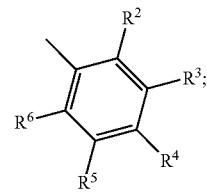

wherein R$^2$, R$^3$, R$^4$, R$^5$ and R$^6$ independent of each other represent hydrogen, halo, R'—SO$_2$—N(R")—, R'—(C═O)—, R'R"N—(C═O)—, cyano, trifluoromethyl, trifluoromethoxy, alkyl or alkoxy or —(CR'R")$_n$—R$^e$.

In a further embodiment of R$^d$, R$^2$ represents R'—SO$_2$—N(R")—; and R$^3$, R$^4$, R$^5$ and R$^6$ each represent hydrogen. In a special embodiment, R$^2$ represents alkylsulfonylamino, such as methylsulfonylamino.

In a still further embodiment of R$^d$, R$^2$ represents R'—(C═O)—; and R$^3$, R$^4$, R$^5$ and R$^6$ each represent hydrogen. In a special embodiment, R$^2$ represents alkylcarbonyl, such as acetyl.

In a further embodiment of R$^d$, R$^2$ and R$^6$ independent of each other represent alkoxy; and R$^3$, R$^4$ and R$^5$ each represent hydrogen. In a special embodiment, R$^2$ represents methoxy. In a further embodiment, R$^6$ represents methoxy. In a still further embodiment, R$^2$ and R$^5$ both represent methoxy.

In a still further embodiment of R$^d$, R$^2$ and R$^3$ independent of each other represent alkoxy; and R$^4$, R$^5$ and R$^6$ each represent hydrogen. In a special embodiment, R$^2$ represents methoxy. In a further embodiment, R$^3$ represents methoxy. In a still further embodiment, R$^2$ and R$^3$ both represent methoxy.

In a further embodiment of R$^d$, R$^2$ and R$^4$ independent of each other represent alkoxy; and R$^3$, R$^5$ and R$^6$ each represent hydrogen. In a special embodiment, R$^2$ represents methoxy. In a further embodiment, R$^4$ represents methoxy. In a still further embodiment, R$^2$ and R$^4$ both represent methoxy.

In a still further embodiment of R$^d$, R$^2$ represents alkoxy; R$^3$ represents halo; and R$^4$, R$^5$ and R$^6$ each represent hydrogen. In a special embodiment, R$^2$ represents methoxy. In a further embodiment, R$^3$ represents fluoro or chloro.

In a further embodiment of R$^d$, R$^2$ represents alkoxy; R$^4$ represents halo; and R$^3$, R$^5$ and R$^6$ each represent hydrogen. In a special embodiment, R$^2$ represents methoxy. In a further embodiment, R$^4$ represents fluoro.

In a still further embodiment of R$^d$, R$^2$ represents alkoxy; R$^5$ represents halo; and R$^3$, R$^4$ and R$^5$ each represent hydrogen. In a special embodiment, R$^2$ represents methoxy. In a further embodiment, R$^5$ represents fluoro.

In a further embodiment of R$^d$, R$^2$ represents alkoxy; R$^6$ represents halo; and R$^3$, R$^4$ and R$^5$ each represent hydrogen. In a special embodiment, R$^2$ represents methoxy. In a further embodiment, R$^6$ represents fluoro or chloro.

In a still further embodiment of R$^d$, R$^2$ represents alkoxy; R$^5$ and R$^6$ independent of each other represent halo; and R$^3$ and R$^4$ each represent hydrogen. In a special embodiment, R$^2$ represents methoxy. In a further embodiment, R$^5$ represents fluoro. In a still further embodiment, R$^6$ represents fluoro.

In a further embodiment of R$^d$, R$^2$ represents alkoxy; R$^3$ and R$^5$ independent of each other represent halo; and R$^4$ and R$^6$ each represent hydrogen. In a special embodiment, R$^2$ represents methoxy. In a further embodiment, R$^3$ represents fluoro. In a still further embodiment, R$^5$ represents fluoro.

In a still further embodiment of R$^d$, R$^2$ represents halo; R$^5$ represents cyano; and R$^3$, R$^4$ and R$^6$ each represent hydrogen. In a special embodiment, R$^2$ represents chloro.

In a further embodiment of $R^d$, $R^2$ represents R'R"N—(C=O)—; and $R^3$, $R^4$, $R^5$ and $R^6$ each represent hydrogen. In a special embodiment, $R^2$ represents aminocarbonyl.

In a still further embodiment of $R^d$, $R^2$ represents hydroxy; $R^3$ represents halo; and $R^4$, $R^5$ and $R^6$ each represent hydrogen. In a special embodiment, $R^3$ represents chloro.

In a further embodiment of $R^d$, $R^2$ represents cyano and $R^3$ or $R^4$ represents halo, such as fluoro. In a special embodiment, $R^2$ represents cyano and $R^3$ represents halo, such as fluoro, and $R^4$, $R^5$ and $R^6$ each represent hydrogen. In a further embodiment, $R^2$ represents cyano and $R^4$ represents halo, such as fluoro, and $R^3$, $R^5$ and $R^6$ each represent hydrogen.

In a further embodiment of $R^d$, $R^2$ represents cyano, $R^4$ represents trifluoromethyl, and $R^3$, $R^5$ and $R^6$ each represent hydrogen.

In a still further embodiment of $R^d$, $R^2$, $R^3$ and $R^6$ independent of each other represents halo; and $R^4$ and $R^5$ each represent hydrogen. In a special embodiment, $R^2$ represents fluoro. In a further embodiment, $R^3$ represents chloro. In still a further embodiment, $R^6$ represents fluoro.

In a still further embodiment of $R^d$, $R^2$ and $R^6$ independent of each other represents halo; and $R^3$, $R^4$ and $R^5$ each represent hydrogen. In a special embodiment, $R^2$ represents chloro or fluoro. In still a further embodiment, $R^6$ represents chloro or fluoro.

In a still further embodiment of $R^d$, $R^2$ and $R^6$ independent of each other represents halo; $R^3$ represents alkyl; and $R^4$ and $R^5$ each represent hydrogen. In a special embodiment, $R^2$ represents chloro or fluoro. In a further embodiment, $R^3$ represents methyl. In still a further embodiment, $R^6$ represents chloro or fluoro.

In a still further embodiment of $R^d$, $R^2$ represents —(CR'R")$_n$—$R^e$; and $R^3$, $R^4$, $R^5$ and $R^6$ each represent hydrogen. In one embodiment, n is 0. In second embodiment, n is 1, and R' and R" represent hydrogen. In a special embodiment, $R^2$ represents morpholin-4-ylmethyl. In a further special embodiment, $R^2$ represents piperazin-1-yl.

In a further embodiment, $R^d$ represents phenyl substituted with methylenedioxy. In a special embodiment, $R^d$ represents benzo[1,3]dioxol-4-yl.

In a special embodiment, wherein $R^d$ represents a substituent selected from the group consisting of: phenyl, 2-methoxyphenyl, 2-methoxy-3-chloro-phenyl, 2-methoxy-3-fluoro-phenyl, 2-methoxy-4-fluoro-phenyl, 2-methoxy-5-chloro-phenyl, 2-methoxy-5-fluoro-phenyl, 2-methoxy-6-fluoro-phenyl, 2-methoxy-6-chloro-phenyl, 2,3-difluoro-6-methoxy-phenyl, 3,5-difluoro-2-methoxy-phenyl, 2-methylsulfonylamino-phenyl, 2-cyanophenyl, 4-fluoro-phenyl, 2-fluoro-phenyl, 2-trifluoromethoxyphenyl, 2-chloro-5-cyano-phenyl, 2-hydroxy-3-chloro-phenyl, 2,6-dichlorophenyl, 2,6-difluorophenyl, 3-chloro-2,6-difluoro-phenyl, 2-chloro-6-fluoro-3-methyl-phenyl, 2-fluoro-6-chloro-3-methyl-phenyl, 2-acetylphenyl, 2-trifluoromethoxy-phenyl, 2-aminocarbonyl-phenyl, 2,3-dimethoxy-phenyl, 2,4-dimethoxy-phenyl, 2,6-dimethoxy-phenyl, 2-(morpholin-4-yl-methyl)-phenyl, 2-piperazin-1-yl-phenyl, 2-cyano-3-fluoro-phenyl, 2-cyano-4-fluoro-phenyl, 2-cyano-4-trifluoromethyl-phenyl, and benzo[1,3]dioxol-4-yl.

In a special embodiment the chemical compound of the invention is 1-(1-Biphenyl-3-yl-1H-benzoimidazol-5-yl)-ethylamine;
1-[1-(2'-Methoxy-biphenyl-3-yl)-1H-benzoimidazol-5-yl]-ethylamine;
3'-[5-(1-Amino-ethyl)-benzoimidazol-1-yl]-biphenyl-2-carbonitrile;
1-[1-(4'-Fluoro-biphenyl-3-yl)-1H-benzoimidazol-5-yl]-ethylamine;
1-[1-(2'-Fluoro-biphenyl-3-yl)-1H-benzoimidazol-5-yl]-ethylamine;
1-[1-(5'-Fluoro-2'-methoxy-biphenyl-3-yl)-1H-benzoimidazol-5-yl]-ethylamine;
1-[1-(2'-Trifluoromethoxy-biphenyl-3-yl)-1H-benzoimidazol-5-yl]-ethylamine;
N-[1-(1-Biphenyl-3-yl-1H-benzoimidazol-5-yl)-ethyl]-acetamide;
N-[1-(1-Biphenyl-3-yl-1H-benzoimidazol-5-yl)-ethyl]-formamide;
N-{1-[1-(5'-Fluoro-2'-methoxy-biphenyl-3-yl)-1H-benzoimidazol-5-yl]-ethyl}-acetamide;
N-{1-[1-(5'-Fluoro-2'-methoxy-biphenyl-3-yl)-1H-benzoimidazol-5-yl]-ethyl}-formamide;
N-[(R)-1-(1-Biphenyl-3-yl-1H-benzoimidazol-5-yl)-ethyl]-acetamide;
N-{(R)-1-[1-(2'-Methoxy-biphenyl-3-yl)-1H-benzoimidazol-5-yl]-ethyl}-acetamide;
N-{(R)-1-[1-(5'-Chloro-2'-methoxy-biphenyl-3-yl)-1H-benzoimidazol-5-yl]-ethyl}-acetamide;
N-{(R)-1-[1-(2'-Methanesulfonylamino-biphenyl-3-yl)-1H-benzoimidazol-5-yl]-ethyl}-acetamide;
N-{(R)-1-[1-(2'-Cyano-biphenyl-3-yl)-1H-benzoimidazol-5-yl]-ethyl}-acetamide;
N-{(R)-1-[1-(2'-Acetyl-biphenyl-3-yl)-1H-benzoimidazol-5-yl]-ethyl}-acetamide;
N-{(S)-1-[1-(2'-Methoxy-biphenyl-3-yl)-1H-benzoimidazol-5-yl]-ethyl}-acetamide;
N-{(S)-1-[1-(2'-Cyano-biphenyl-3-yl)-1H-benzoimidazol-5-yl]-ethyl}-acetamide;
N-[(S)-1-(1-Biphenyl-3-yl-1H-benzoimidazol-5-yl)-acetamide;
N-{(S)-1-[1-(5'-Chloro-2'-methoxy-biphenyl-3-yl)-1H-benzoimidazol-5-yl]-ethyl}-acetamide;
N-{(S)-1-[1-(2'-Methanesulfonylamino-biphenyl-3-yl)-1H-benzoimidazol-5-yl]-ethyl}-acetamide;
N-{(S)-1-[1-(2'-Acetyl-biphenyl-3-yl)-1H-benzoimidazol-5-yl]-ethyl}-acetamide;
N-{(R)-1-[1-(3-Benzo[1,3]dioxol-4-yl-phenyl)-1H-benzoimidazol-5-yl]-ethyl}-acetamide;
N-{(S)-1-[1-(3-Benzo[1,3]dioxol-4-yl-phenyl)-1H-benzoimidazol-5-yl]-ethyl}-acetamide;
(R)-1-(1-Biphenyl-3-yl-1H-benzoimidazol-5-yl)-ethylamine;
(R)-1-[1-(2'-Methoxy-biphenyl-3-yl)-1H-benzoimidazol-5-yl]-ethylamine;
(R)-1-[1-(5'-Chloro-2'-methoxy-biphenyl-3-yl)-1H-benzoimidazol-5-yl]-ethylamine;
N-{3'-[5-((R)-1-Amino-ethyl)-benzoimidazol-1-yl]-biphenyl-2-yl}-methanesulfonamide;
3'-[5-((R)-1-Amino-ethyl)-benzoimidazol-1-yl]-biphenyl-2-carbonitrile;
(R)-1-[1-(2',6'-Dimethoxy-biphenyl-3-yl)-1H-benzoimidazol-5-yl]-ethylamine;
(R)-1-[1-(3'-Fluoro-2'-methoxy-biphenyl-3-yl)-1H-benzoimidazol-5-yl]-ethylamine;
(R)-1-[1-(2',3'-Dimethoxy-biphenyl-3-yl)-1H-benzoimidazol-5-yl]-ethylamine;
(R)-1-[1-(6'-Fluoro-2'-methoxy-biphenyl-3-yl)-1H-benzoimidazol-5-yl]-ethylamine;
(R)-1-[1-(3'-Chloro-2'-methoxy-biphenyl-3-yl)-1H-benzoimidazol-5-yl]-ethylamine;
(R)-1-[1-(2',4'-Dimethoxy-biphenyl-3-yl)-1H-benzoimidazol-5-yl]-ethylamine;

(R)-1-[1-(3-Benzo[1,3]dioxol-4-yl-phenyl)-1H-benzoimidazol-5-yl]-ethylamine;
(R)-1-[1-(2',3'-Difluoro-6'-methoxy-biphenyl-3-yl)-1H-benzoimidazol-5-yl]-ethylamine;
(R)-1-[1-(4'-Fluoro-2'-methoxy-biphenyl-3-yl)-1H-benzoimidazol-5-yl]-ethylamine;
3'-[5-((R)-1-Amino-ethyl)-benzoimidazol-1-yl]-6-chloro-biphenyl-3-carbonitrile;
3'-[5-((R)-1-Amino-ethyl)-benzoimidazol-1-yl]-3-chloro-biphenyl-2-ol;
(R)-1-[1-(3'-Chloro-2',6'-difluoro-biphenyl-3-yl)-1H-benzoimidazol-5-yl]-ethylamine;
(R)-1-[1-(2'-Morpholin-4-ylmethyl-biphenyl-3-yl)-1H-benzoimidazol-5-yl]-ethylamine;
(R)-1-[1-(3',5'-Difluoro-2'-methoxy-biphenyl-3-yl)-1H-benzoimidazol-5-yl]-ethylamine;
(R)-1-[1-(5'-Fluoro-2'-methoxy-biphenyl-3-yl)-1H-benzoimidazol-5-yl]-ethylamine;
(R)-1-[1-(6'-Chloro-2'-methoxy-biphenyl-3-yl)-1H-benzoimidazol-5-yl]-ethylamine;
(R)-1-[1-(2'-Chloro-6'-fluoro-3'-methyl-biphenyl-3-yl)-1H-benzoimidazol-5-yl]-ethylamine;
(R)-1-[1-(2',6'-Dichloro-biphenyl-3-yl)-1H-benzoimidazol-5-yl]-ethylamine;
(R)-1-[1-(2'-piperazin-1-yl-biphenyl-3-yl)-1H-benzoimidazol-5-yl]-ethylamine;
(R)-1-[1-(2',6'-Difluoro-biphenyl-3-yl)-1H-benzoimidazol-5-yl]-ethylamine;
(R)-1-[1-(2'-Chloro-6'-fluoro-5'-methyl-biphenyl-3-yl)-1H-benzoimidazol-5-yl]-ethylamine;
3'-[5-((R)-1-Amino-ethyl)-benzoimidazol-1-yl]-biphenyl-2-carboxylic acid amide;
1-{3'-[5-((R)-1-Amino-ethyl)-benzoimidazol-1-yl]-biphenyl-2-yl}-ethanone;
(R)-1-[1-(2'-Trifluoromethoxy-biphenyl-3-yl)-1H-benzoimidazol-5-yl]-ethylamine;
(S)-1-(1-Biphenyl-3-yl-1H-benzoimidazol-5-yl)-ethylamine;
(S)-1-[1-(2'-Methoxy-biphenyl-3-yl)-1H-benzoimidazol-5-yl]-ethylamine;
3'-[5-((S)-1-Amino-ethyl)-benzoimidazol-1-yl]-biphenyl-2-carboxylic acid amide;
3'-[5-((S)-1-Amino-ethyl)-benzoimidazol-1-yl]-biphenyl-2-carbonitrile;
1-{3'-[5-((S)-1-Amino-ethyl)-benzoimidazol-1-yl]-biphenyl-2-yl}-ethanone;
(S)-1-[1-(2'-Trifluoromethoxy-biphenyl-3-yl)-1H-benzoimidazol-5-yl]-ethylamine;
(S)-1-[1-(3-Benzo[1,3]dioxol-4-yl-phenyl)-1H-benzoimidazol-5-yl]-ethylamine;
(S)-1-[1-(2',3'-Difluoro-6'-methoxy-biphenyl-3-yl)-1H-benzoimidazol-5-yl]-ethylamine;
(S)-1-[1-(4'-Fluoro-2'-methoxy-biphenyl-3-yl)-1H-benzoimidazol-5-yl]-ethylamine;
3'-[5-((S)-1-Amino-ethyl)-benzoimidazol-1-yl]-6-chloro-biphenyl-3-carbonitrile;
3'-[5-((S)-1-Amino-ethyl)-benzoimidazol-1-yl]-3-chloro-biphenyl-2-ol;
(S)-1-[1-(3'-Chloro-2',6'-difluoro-biphenyl-3-yl)-1H-benzoimidazol-5-yl]-ethylamine;
(S)-1-[1-(2'-Morpholin-4-ylmethyl-biphenyl-3-yl)-1H-benzoimidazol-5-yl]-ethylamine;
(S)-1-[1-(3',5'-Difluoro-2'-methoxy-biphenyl-3-yl)-1H-benzoimidazol-5-yl]-ethylamine;
(S)-1-[1-(2',6'-Dimethoxy-biphenyl-3-yl)-1H-benzoimidazol-5-yl]-ethylamine;
(S)-1-[1-(3'-Fluoro-2'-methoxy-biphenyl-3-yl)-1H-benzoimidazol-5-yl]-ethylamine;
(S)-1-[1-(6'-Fluoro-2'-methoxy-biphenyl-3-yl)-1H-benzoimidazol-5-yl]-ethylamine;
(S)-1-[1-(6'-Chloro-2'-methoxy-biphenyl-3-yl)-1H-benzoimidazol-5-yl]-ethylamine;
(S)-1-[1-(2'-Chloro-6'-fluoro-3'-methyl-biphenyl-3-yl)-1H-benzoimidazol-5-yl]-ethylamine;
(S)-1-[1-(2',4'-Dimethoxy-biphenyl-3-yl)-1H-benzoimidazol-5-yl]-ethylamine;
(S)-1-[1-(2',3'-Dimethoxy-biphenyl-3-yl)-1H-benzoimidazol-5-yl]-ethylamine;
(S)-1-[1-(2',6'-Dichloro-biphenyl-3-yl)-1H-benzoimidazol-5-yl]-ethylamine;
(S)-1-[1-(2'-piperazin-1-yl-biphenyl-3-yl)-1H-benzoimidazol-5-yl]-ethylamine;
(S)-1-[1-(2',6'-Difluoro-biphenyl-3-yl)-1H-benzoimidazol-5-yl]-ethylamine;
(S)-1-[1-(2'-Chloro-6'-fluoro-5'-methyl-biphenyl-3-yl)-1H-benzoimidazol-5-yl]-ethylamine;
(S)-1-[1-(5'-Fluoro-2'-methoxy-biphenyl-3-yl)-1H-benzoimidazol-5-yl]-ethylamine;
3'-[5-((R)-1-Amino-ethyl)-benzoimidazol-1-yl]-4-trifluoromethyl-biphenyl-2-carbonitrile;
3'-[5-((S)-1-Amino-ethyl)-benzoimidazol-1-yl]-4-trifluoromethyl-biphenyl-2-carbonitrile;
3'-[5-((R)-1-Amino-ethyl)-benzoimidazol-1-yl]-3-fluoro-biphenyl-2-carbonitrile;
3'-[5-((S)-1-Amino-ethyl)-benzoimidazol-1-yl]-3-fluoro-biphenyl-2-carbonitrile;
N-{(R)-1-[1-(2'-Cyano-4'-fluoro-biphenyl-3-yl)-1H-benzoimidazol-5-yl]ethyl}-acetamide;
N-{(S)-1-[1-(2'-Cyano-4'-fluoro-biphenyl-3-yl)-1H-benzoimidazol-5-yl]ethyl}-acetamide;
3'-[5-((R)-1-Amino-ethyl)-benzoimidazol-1-yl]-4-fluoro-biphenyl-2-carbonitrile;
3'-[5-((S)-1-Amino-ethyl)-benzoimidazol-1-yl]-4-fluoro-biphenyl-2-carbonitrile;
or an N-oxide thereof, any of its isomers or any mixture of its isomers,
or a pharmaceutically acceptable salt thereof.

Any combination of two or more of the embodiments as described above is considered within the scope of the present invention.

Definition of Substituents

In the context of this invention halo represents fluoro, chloro, bromo or iodo.

In the context of this invention an alkyl group designates a univalent saturated, straight or branched hydrocarbon chain. The hydrocarbon chain preferably contain of from one to six carbon atoms ($C_{1-6}$-alkyl), including pentyl, isopentyl, neopentyl, tertiary pentyl, hexyl and isohexyl. In a preferred embodiment alkyl represents a $C_{1-4}$-alkyl group, including butyl, isobutyl, secondary butyl, and tertiary butyl. In another preferred embodiment of this invention alkyl represents a $C_{1-3}$-alkyl group, which may in particular be methyl, ethyl, propyl or isopropyl.

In the context of this invention an alkenyl group designates a carbon chain containing one or more double bonds, including di-enes, tri-enes and poly-enes. In a preferred embodiment the alkenyl group of the invention comprises of from two to six carbon atoms ($C_{2-4}$-alkenyl), including at least one double bond. In a most preferred embodiment the alkenyl group of the invention is ethenyl; 1- or 2-propenyl; 1-, 2- or 3-butenyl, or 1,3-butadienyl; 1-, 2-, 3-, 4- or 5-hexenyl, or 1,3-hexadienyl, or 1,3,5-hexatrienyl.

In the context of this invention an alkynyl group designates a carbon chain containing one or more triple bonds, including di-ynes, tri-ynes and poly-ynes. In a preferred embodiment the alkynyl group of the invention comprises of from two to six carbon atoms ($C_{2-6}$-alkynyl), including at least one triple bond. In its most preferred embodiment the alkynyl group of the invention is ethynyl; 1-, or 2-propynyl; 1-, 2-, or 3-butynyl, or 1,3-butadiynyl; 1-, 2-, 3-, 4-pentynyl, or 1,3-pentadiynyl; 1-, 2-, 3-, 4-, or 5-henynyl, or 1,3-hexadiynyl or 1,3,5-hexatriynyl.

In the context of this invention a cycloalkyl group designates a cyclic alkyl group, preferably containing of from three to seven carbon atoms ($C_{3-7}$-cycloalkyl), including cyclopropyl, cyclobutyl, cyclopentyl, cyclohexyl and cycloheptyl.

Alkoxy means O-alkyl, wherein alkyl is as defined above.

Alkoxyalkyl means alkoxy as above and alkyl as above, meaning for example, methoxymethyl.

Cycloalkoxy means O-cycloalkyl, wherein cycloalkyl is as defined above.

Cycloalkylalkyl means cycloalkyl as above and alkyl as above, meaning for example, cyclopropylmethyl.

In the context of this invention an aryl group designates a carbocyclic aromatic ring system such as phenyl, naphthyl (1-naphthyl or 2-naphthyl) or fluorenyl.

In the context of this invention a heterocyclic ring designates a monocyclic heterocyclic group, which holds one or more heteroatoms in its ring. Preferred heteroatoms include nitrogen (N), oxygen (O), and sulphur (S). The ring may in particular be aromatic (i.e. a heteroaryl), saturated or partially saturated. Examples of preferred saturated or partially saturated monocyclic heterocyclic 5-membered groups of the invention include 1,3-dioxolan, imidazoline, imidazolidine, oxazoline, oxazolidine, oxadiazoline, pyrroline, pyrrolidine, pyrazolidine, and pyrazoline.

Examples of preferred saturated or partially saturated monocyclic heterocyclic 6-membered groups of the invention include 1,4-dioxolane, 1,4-dithiane, morpholine, 1,4-oxazine, oxadiazine, piperidine, piperazine, dihydro-pyrane, tetrahydro-pyrane, thiomorpholine, 1,3,5-trithiane.

Examples of preferred saturated or partially saturated monocyclic heterocyclic 7-membered groups of the invention include homopiperidine and homopiperazine.

Examples of preferred monocyclic heteroaryl groups of the invention include aromatic 5- and 6-membered monocyclic heterocyclic groups, including for example, but not limited to, oxazolyl, isoxazolyl, thiazolyl, isothiazolyl, tetrazolyl, 1,2,4-oxadiazolyl, 1,2,5-oxadiazolyl, 1,3,4-oxadiazolyl, triazolyl, 1,2,4-thiadiazolyl, 1,2,5-thiadiazolyl, imidazolyl, pyrrolyl, pyrazolyl, furanyl, thienyl, pyridyl, pyrimidyl, or pyridazinyl.

Pharmaceutically Acceptable Salts

The chemical compound of the invention may be provided in any form suitable for the intended administration. Suitable forms include pharmaceutically (i.e. physiologically) acceptable salts, and pre- or prodrug forms of the chemical compound of the invention.

Examples of pharmaceutically acceptable addition salts include, without limitation, the non-toxic inorganic and organic acid addition salts such as the hydro-chloride, the hydrobromide, the nitrate, the perchlorate, the phosphate, the sulphate, the formate, the acetate, the aconate, the ascorbate, the benzenesulphonate, the benzoate, the cinnamate, the citrate, the embonate, the enantate, the fumarate, the glutamate, the glycolate, the lactate, the maleate, the malonate, the mandelate, the methanesulphonate, the naphthalene-2-sulphonate, the phthalate, the salicylate, the sorbate, the stearate, the succinate, the tartrate, the toluene-p-sulphonate, and the like. Such salts may be formed by procedures well known and described in the art.

Other acids such as oxalic acid, which may not be considered pharmaceutically acceptable, may be useful in the preparation of salts useful as intermediates in obtaining a chemical compound of the invention and its pharmaceutically acceptable acid addition salt.

Examples of pharmaceutically acceptable cationic salts of a chemical compound of the invention include, without limitation, the sodium, the potassium, the calcium, the magnesium, the zinc, the aluminium, the lithium, the choline, the lysinium, and the ammonium salt, and the like, of a chemical compound of the invention containing an anionic group. Such cationic salts may be formed by procedures well known and described in the art.

In the context of this invention the "onium salts" of N-containing compounds are also contemplated as pharmaceutically acceptable salts. Preferred "onium salts" include the alkyl-onium salts, the cycloalkyl-onium salts, and the cycloalkylalkyl-onium salts.

Examples of pre- or prodrug forms of the chemical compound of the invention include examples of suitable prodrugs of the substances according to the invention include compounds modified at one or more reactive or derivatizable groups of the parent compound. Of particular interest are compounds modified at a carboxyl group, a hydroxyl group, or an amino group. Examples of suitable derivatives are esters or amides.

The chemical compound of the invention may be provided in dissoluble or indissoluble forms together with a pharmaceutically acceptable solvent such as water, ethanol, and the like. Dissoluble forms may also include hydrated forms such as the monohydrate, the dihydrate, the hemihydrate, the trihydrate, the tetrahydrate, and the like. In general, the dissoluble forms are considered equivalent to indissoluble forms for the purposes of this invention.

Steric Isomers

It will be appreciated by those skilled in the art that the compounds of the present invention may contain one or more chiral centres and that such compounds may exist in different stereoisomeric forms—including enantiomers, diastereomers and cis-trans-isomers.

The invention includes all such isomers and any mixtures thereof including racemic mixtures.

Methods for the resolution of optical isomers, known to those skilled in the art may be used, and will be apparent to the average worker skilled in the art. Such methods include those discussed by J. Jaques, A. Collet, and S. Wilen in "Enantiomers, Racemates, and Resolutions", John Wiley and Sons, New York (1981).

Optical active compounds can also be prepared from optically active starting materials.

N-Oxides

In the context of this invention an N-oxide designates an oxide derivative of a nitrogen containing compound, e.g. N-containing heterocyclic compounds capable of forming such N-oxides, and compounds holding one or more amino groups. For example, the N-oxide of a compound containing a pyridyl may be the 1-oxy-pyridin-2, -3 or -4-yl derivative.

N-oxides of the compounds of the invention may be prepared by oxidation of the corresponding nitrogen base using a conventional oxidizing agent such as hydrogen peroxide in the presence of an acid such as acetic acid at an elevated temperature, or by reaction with a peracid such as peracetic acid in a suitable solvent, e.g. dichloromethane, ethyl acetate or methyl acetate, or in chloroform or dichloromethane with 3-chloroperoxybenzoic acid.

Labelled Compounds

The compounds of the invention may be used in their labelled or unlabelled form. In the context of this invention the labelled compound has one or more atoms replaced by an atom having an atomic mass or mass number different from the atomic mass or mass number usually found in nature. The labelling will allow easy quantitative detection of said compound.

The labelled compounds of the invention may be useful as diagnostic tools, radio tracers, or monitoring agents in various diagnostic methods, and for in vivo receptor imaging.

The labelled isomer of the invention preferably contains at least one radionuclide as a label. Positron emitting radionuclides are all candidates for usage. In the context of this invention the radionuclide is preferably selected from $^2$H (deuterium), $^3$H (tritium), $^{13}$C, $^{14}$C, $^{131}$I, $^{125}$I, $^{123}$I, and $^{18}$F.

The physical method for detecting the labelled isomer of the present invention may be selected from Position Emission Tomography (PET), Single Photon Imaging Computed Tomography (SPECT), Magnetic Resonance Spectroscopy (MRS), Magnetic Resonance Imaging (MRI), and Computed Axial X-ray Tomography (CAT), or combinations thereof.

Methods of Preparation

The chemical compounds of the invention may be prepared by conventional methods for chemical synthesis, e.g. those described in the working examples. The starting materials for the processes described in the present application are known or may readily be prepared by conventional methods from commercially available chemicals.

Also one compound of the invention can be converted to another compound of the invention using conventional methods.

The end products of the reactions described herein may be isolated by conventional techniques, e.g. by extraction, crystallisation, distillation, chromatography, etc.

The compounds of this invention may exist in unsolvated as well as in solvated forms with pharmaceutically acceptable solvents such as water, ethanol and the like. In general, the solvated forms are considered equivalent to the unsolvated forms for the purposes of this invention.

Biological Activity

Compounds of the invention are capable of modulating the $GABA_A$ receptor complex. They may be tested for their ability to bind to the $GABA_A$ receptor complex, including specific subunits thereof.

The compounds of the present invention, being ligands for the benzodiazepine binding site on $GABA_A$ receptors, are therefore of use in the treatment and/or prevention of a variety of disorders of the central nervous system. Thus in further aspect, the compounds of the invention are considered useful for the treatment, prevention or alleviation of a disease, disorder or condition responsive to modulation of the $GABA_A$ receptor complex in the central nervous system.

In a special embodiment, the compounds of the invention are considered useful for the treatment, prevention or alleviation of anxiety disorders, such as panic disorder with or without agoraphobia, agoraphobia without history of panic disorder, animal and other phobias including social phobias, obsessive-compulsive disorder, and generalized or substance-induced anxiety disorder;

stress disorders including post-traumatic and acute stress disorder;

sleep disorders;

memory disorder;

neuroses;

convulsive disorders, for example epilepsy, seizures, convulsions, or febrile convulsions in children;

migraine;

mood disorders;

depressive or bipolar disorders, for example depression, single-episode or recurrent major depressive disorder, dysthymic disorder, bipolar disorder, bipolar I and bipolar II manic disorders, and cyclothymic disorder, psychotic disorders, including schizophrenia;

neurodegeneration arising from cerebral ischemia;

attention deficit hyperactivity disorder;

pain and nociception, e.g. neuropathic pain;

emesis, including acute, delayed and anticipatory emesis, in particular emesis induced by chemotherapy or radiation;

motion sickness, post-operative nausea and vomiting;

eating disorders including anorexia nervosa and bulimia nervosa;

premenstrual syndrome;

neuralgia, e.g. trigeminal neuralgia;

muscle spasm or spasticity, e.g. in paraplegic patients;

the effects of substance abuse or dependency, including alcohol withdrawal;

cognitive disorders, such as Alzheimer's disease;

cerebral ischemia, stroke, head trauma;

tinnitus: and disorders of circadian rhythm, e.g. in subjects suffering from the effects of jet lag or shift work.

Preferably the compounds of the invention are considered useful for the treatment, prevention or alleviation of anxiety disorders, such as panic disorder with or without agoraphobia, agoraphobia without history of panic disorder, animal and other phobias including social phobias, obsessive-compulsive disorder, and generalized or substance-induced anxiety disorder;

Further, the compounds of the invention may be useful as radioligands in assays for detecting compounds capable of binding to the human $GABA_A$ receptor.

It is at present contemplated that a suitable dosage of the active pharmaceutical ingredient (API) is within the range of from about 0.1 to about 1000 mg API per day, more preferred of from about 10 to about 500 mg API per day, most preferred of from about 30 to about 100 mg API per day, dependent, however, upon the exact mode of administration, the form in which it is administered, the indication considered, the subject and in particular the body weight of the subject involved, and further the preference and experience of the physician or veterinarian in charge.

Pharmaceutical Compositions

In another aspect the invention provides novel pharmaceutical compositions comprising a therapeutically effective amount of the chemical compound of the invention.

While a chemical compound of the invention for use in therapy may be administered in the form of the raw chemical compound, it is preferred to introduce the active ingredient, optionally in the form of a physiologically acceptable salt, in a pharmaceutical composition together with one or more adjuvants, excipients, carriers, buffers, diluents, and/or other customary pharmaceutical auxiliaries.

In a preferred embodiment, the invention provides pharmaceutical compositions comprising the chemical compound of the invention, or a pharmaceutically acceptable salt or derivative thereof, together with one or more pharmaceutically acceptable carriers, and, optionally, other therapeutic and/or prophylactic ingredients, known and used in the art.

The carrier(s) must be "acceptable" in the sense of being compatible with the other ingredients of the formulation and not harmful to the recipient thereof.

Pharmaceutical compositions of the invention may be those suitable for oral, rectal, bronchial, nasal, pulmonal, topical (including buccal and sub-lingual), transdermal, vaginal or parenteral (including cutaneous, subcutaneous, intramuscular, intraperitoneal, intravenous, intraarterial, intracerebral, intraocular injection or infusion) administration, or those in a form suitable for administration by inhalation or insufflation, including powders and liquid aerosol administration, or by sustained release systems. Suitable examples of sustained release systems include semipermeable matrices of solid hydrophobic polymers containing the compound of the invention, which matrices may be in form of shaped articles, e.g. films or microcapsules.

The chemical compound of the invention, together with a conventional adjuvant, carrier, or diluent, may thus be placed into the form of pharmaceutical compositions and unit dosages thereof. Such forms include solids, and in particular tablets, filled capsules, powder and pellet forms, and liquids, in particular aqueous or non-aqueous solutions, suspensions, emulsions, elixirs, and capsules filled with the same, all for oral use, suppositories for rectal administration, and sterile injectable solutions for parenteral use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

The chemical compound of the present invention can be administered in a wide variety of oral and parenteral dosage forms. It will be obvious to those skilled in the art that the following dosage forms may comprise, as the active component, either a chemical compound of the invention or a pharmaceutically acceptable salt of a chemical compound of the invention.

For preparing pharmaceutical compositions from a chemical compound of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid, which is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as a mixture of fatty acid glyceride or cocoa butter, is first melted and the active component is dispersed homogeneously therein, as by stirring. The molten homogenous mixture is then poured into convenient sized moulds, allowed to cool, and thereby to solidify.

Compositions suitable for vaginal administration may be presented as pessaries, tampons, creams, gels, pastes, foams or sprays containing in addition to the active ingredient such carriers as are known in the art to be appropriate.

Liquid preparations include solutions, suspensions, and emulsions, for example, water or water-propylene glycol solutions. For example, parenteral injection liquid preparations can be formulated as solutions in aqueous polyethylene glycol solution.

The chemical compound according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavours, stabilising and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations, intended for conversion shortly before use to liquid form preparations for oral administration. Such liquid forms include solutions, suspensions, and emulsions. In addition to the active component such preparations may comprise colorants, flavours, stabilisers, buffers, artificial and natural sweeteners, dispersants, thickeners, solubilizing agents, and the like.

For topical administration to the epidermis the chemical compound of the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Compositions suitable for topical administration in the mouth include lozenges comprising the active agent in a flavoured base, usually sucrose and acacia or tragacanth; pastilles comprising the active ingredient in an inert base such as gelatin and glycerine or sucrose and acacia; and mouthwashes comprising the active ingredient in a suitable liquid carrier.

Solutions or suspensions are applied directly to the nasal cavity by conventional means, for example with a dropper, pipette or spray. The compositions may be provided in single or multi-dose form.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In compositions intended for administration to the respiratory tract, including intranasal compositions, the compound will generally have a small particle size for example of the order of 5 microns or less. Such a particle size may be obtained by means known in the art, for example by micronization.

When desired, compositions adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration and continuous infusion are preferred compositions.

Further details on techniques for formulation and administration may be found in the latest edition of *Remington's Pharmaceutical Sciences* (Maack Publishing Co., Easton, Pa.).

A therapeutically effective dose refers to that amount of active ingredient, which ameliorates the symptoms or condition. Therapeutic efficacy and toxicity, e.g. $ED_{50}$ and $LD_{50}$, may be determined by standard pharmacological procedures in cell cultures or experimental animals. The dose ratio between therapeutic and toxic effects is the therapeutic index and may be expressed by the ratio $LD_{50}/ED_{50}$. Pharmaceutical compositions exhibiting large therapeutic indexes are preferred.

The dose administered must of course be carefully adjusted to the age, weight and condition of the individual being treated, as well as the route of administration, dosage form and regimen, and the result desired, and the exact dosage should of course be determined by the practitioner.

The actual dosage depends on the nature and severity of the disease being treated, and is within the discretion of the physician, and may be varied by titration of the dosage to the particular circumstances of this invention to produce the desired therapeutic effect. However, it is presently contemplated that pharmaceutical compositions containing of from about 0.1 to about 500 mg of active ingredient per individual dose, preferably of from about 1 to about 100 mg, most preferred of from about 1 to about 10 mg, are suitable for therapeutic treatments.

The active ingredient may be administered in one or several doses per day. A satisfactory result can, in certain instances, be obtained at a dosage as low as 0.1 μg/kg i.v. and 1 μg/kg p.o. The upper limit of the dosage range is presently considered to be about 10 mg/kg i.v. and 100 mg/kg p.o. Preferred ranges are from about 0.1 μg/kg to about 10 mg/kg/day i.v., and from about 1 μg/kg to about 100 mg/kg/day p.o.

Methods of Therapy

In another aspect the invention provides a method for the treatment, prevention or alleviation of a disease or a disorder or a condition of a living animal body, including a human, which disease, disorder or condition is responsive to modulation of the $GABA_A$ receptor complex in the central nervous system, and which method comprises administering to such a living animal body, including a human, in need thereof an effective amount of a chemical compound of the invention.

It is at present contemplated that suitable dosage ranges are 0.1 to 1000 milligrams daily, 10-500 milligrams daily, and especially 30-100 milligrams daily, dependent as usual upon the exact mode of administration, form in which administered, the indication toward which the administration is directed, the subject involved and the body weight of the subject involved, and further the preference and experience of the physician or veterinarian in charge.

EXAMPLES

The invention is further illustrated with reference to the following examples, which are not intended to be in any way limiting to the scope of the invention as claimed.

General: All reactions involving air sensitive reagents or intermediates were performed under nitrogen and in anhydrous solvents. Magnesium sulphate or sodium sulphate was used as drying agent in the workup-procedures and solvents were evaporated under reduced pressure.

Example 1

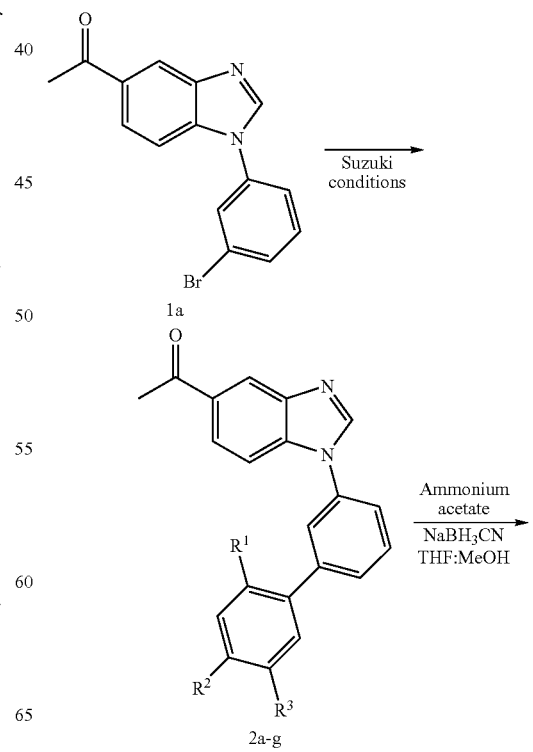

(General Scheme 1)

-continued

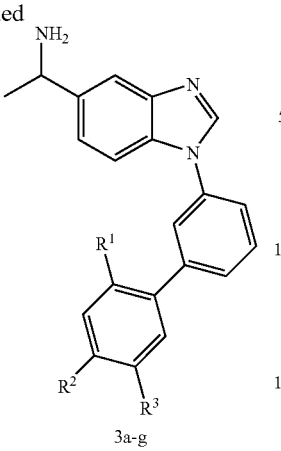

3a-g

General Procedure for the Synthesis of 3a-g

Ethanone, 1-[1-(3-bromophenyl)-1H-benzimidazol-5-yl] (may be prepared as described in WO 96/33191) 1a, (0.6 g, 2 mmol) was dissolved in 8 ml Suzuki solvent (7:3:2 DME:Water:EtOH) and 1 ml 2M $Na_2CO_3$.

To this solution was added 2.2 mmol arylboronic acid and 0.02 mmol $PdCl_2(PPH_3)_2$. The reaction was subjected to microwave heating for 160° C. for 240 sec. After cooling the reaction mixture was poured into water and extracted with EtOAc. The organic phase was dried ($MgSO_4$) and evaporated.

The crude mixture was reductively aminated by redissolving in 20 ml THF:MeOH 1:1 followed by addition of $NaBH_3CN$ (4 mmol) and ammonium acetate (1.7 g, 22 mmol). The reaction was stirred at 60° C. overnight after which LCMS was used to monitor if the reaction had finished. After cooling the reaction mixture was evaporated and purified by column chromatography eluting with a mixture of dichloromethane, methanol and ammonia (90:10:1 v/v/v). Evaporation of the pure fractions gave the pure material. If the product was an oil it was redissolved in a minimum amount of THF and precipitated as a hydrochloride salt using 3M HCl in TBME.

The following compounds were prepared by the above methodology:

1-(1-Biphenyl-3-yl-1H-benzoimidazol-5-yl)-ethylamine, hydrochloride (3a)
  HRMS: Calc: $C_{21}H_{20}N_3$ (M+H$^+$)=314.1657. Found: $C_{21}H_{22}N_3$ (M+H$^+$)=314.1659.
1-[1-(2'-Methoxy-biphenyl-3-yl)-1H-benzoimidazol-5-yl]-ethylamine, hydrochloride (3b)
  HRMS: Calc: $C_{22}H_{22}N_3O$ (M+H$^+$)=344.1763. Found: $C_{22}H_{22}N_3O$ (M+H$^+$)=344.1774.
3'-[5-(1-Amino-ethyl)-benzoimidazol-1-yl]-biphenyl-2-carbonitrile (3c)
  HRMS: Calc: $C_{22}H_{19}N_4$ (M+H$^+$)=339.1610. Found: $C_{22}H_{19}N_4$ (M+H$^+$)=339.1595.
1-[1-(4'-Fluoro-biphenyl-3-yl)-1H-benzoimidazol-5-yl]-ethylamine, hydrochloride (3d)
  HRMS: Calc: $C_{21}H_{19}N_3F$ (M+H$^+$)=332.1563. Found: $C_{21}H_{19}N_4F$ (M+H$^+$)=332.1547.
1-[1-(2'-Fluoro-biphenyl-3-yl)-1H-benzoimidazol-5-yl]-ethylamine, hydrochloride (3e)
  HRMS: Calc: $C_{21}H_{19}N_3F$ (M+H$^+$)=332.1563. Found: $C_{21}H_{19}N_4F$ (M+H$^+$)=332.1557.
1-[1-(5'-Fluoro-2'-methoxy-biphenyl-3-yl)-1H-benzoimidazol-5-yl]-ethylamine, hydrochloride (3f)
  HRMS: Calc: $C_{22}H_{21}N_3OF$ (M+H$^+$)=362.1669. Found: $C_{22}H_{21}N_3OF$ (M+H$^+$)=362.1661.
1-[1-(2'-Trifluoromethoxy-biphenyl-3-yl)-1H-benzoimidazol-5-yl]-ethylamine, hydrochloride (3g)
  HRMS: Calc: $C_{22}H_{19}N_3OF_3$ (M+H$^+$)=398.1480. Found: $C_{22}H_{19}N_3OF_3$ (M+H$^+$)=398.1467.

Example 2

(General Scheme 2)

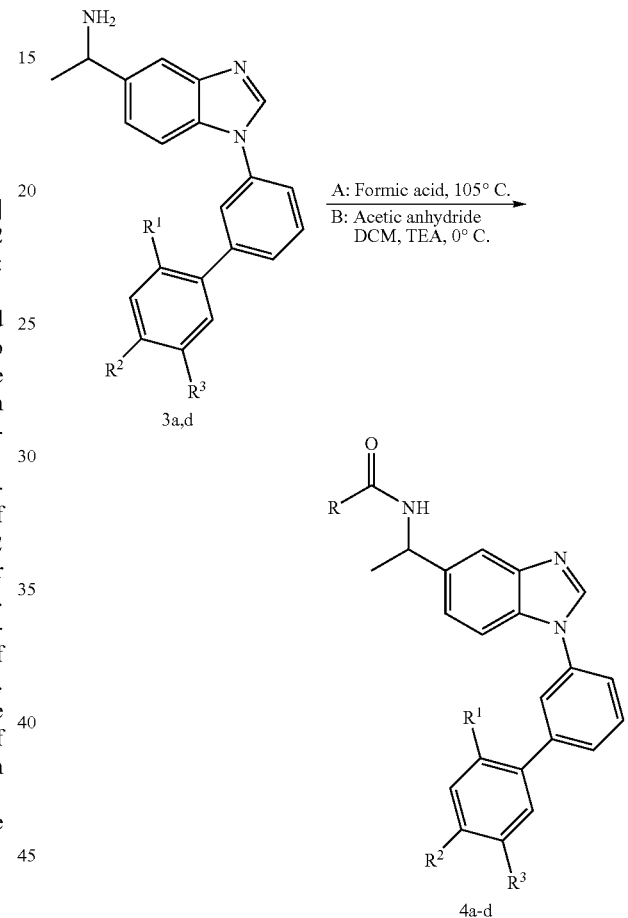

Example on Method A 1-(1-Biphenyl-3-yl-1H-benzoimidazol-5-yl)-ethylamine 3a (0.3 g, 0.75 mmol) was dissolved in 5 ml formic acid and heated at 105° C. overnight. TLC and LCMS show complete conversion, and the solvent was evaporated. The oil was dissolved in DCM and washed with $Na_2CO_3$ sat. The organic phase was dried evaporated and subjected to column chromatography eluting with a mixture of dichloromethane, methanol and ammonia (90:10:1 v/v/v). This gave the product as a white solid in 34% yield.

Example on Method B 1-(1-Biphenyl-3-yl-1H-benzoimidazol-5-yl)-ethylamine 3a (0.3 g, 0.75 mmol) was dissolved in 10 ml DCM and triethylamine (0.75 mmol) was added. The solution was cooled to 0° C. where acetic acid anhydride (1.5 eqv.) was added dropwise. After stirring for 3 h the reaction mixture was allowed to warm to RT and then 10 ml Na$_2$CO$_3$ sat was added. The two phases were separated and the organic phase dried with MgSO$_4$. Column chromatography eluting with a mixture of dichloromethane, methanol and ammonia (90:10:1 v/v/v), gave the product as a white solid in 41% yield.

The following compounds were prepared by the methodology of Methods A and B:

N-[1-(1-Biphenyl-3-yl-1H-benzoimidazol-5-yl)-ethyl]-acetamide (4a)

The compound was prepared from 3a according to method B.

HRMS: Calc: C$_{23}$H$_{22}$N$_3$O (M+H$^+$)=356.1763. Found: C$_{23}$H$_{22}$N$_3$O (M+H$^+$)=356.1754.

N-[1-(1-Biphenyl-3-yl-1H-benzoimidazol-5-yl)-ethyl]-formamide (4b)

The compound was prepared from 3a according to method A.

HRMS: Calc: C$_{22}$H$_{20}$N$_3$O (M+H$^+$)=342.1606. Found: C$_{22}$H$_{20}$N$_3$O (M+H$^+$)=342.1595.

N-{1-[1-(5'-Fluoro-2'-methoxy-biphenyl-3-yl)-1H-benzoimidazol-5-yl]-ethyl}-acetamide (4c)

The compound was prepared from 3f according to method B.

HRMS: Calc: C$_{24}$H$_{23}$N$_3$O$_2$F (M+H$^+$)=404.1774. Found: C$_{24}$H$_{23}$N$_3$O$_2$F (M+H$^+$)=404.1782.

N-{1-[1-(5'-Fluoro-2'-methoxy-biphenyl-3-yl)-1H-benzoimidazol-5-yl]-ethyl}-formamide (4d)

The compound was prepared from 3f according to method A.

HRMS: Calc: C$_{23}$H$_{21}$N$_3$O$_2$F (M+H$^+$)=390.1618. Found: C$_{23}$H$_{21}$N$_3$O$_2$F (M+H$^+$)=390.1601.

Example 3

Synthesis of optically active analogues

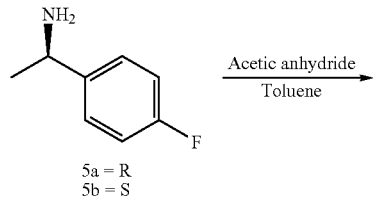

5a = R
5b = S

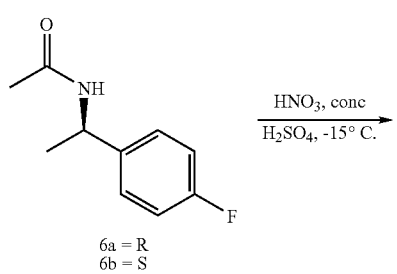

6a = R
6b = S

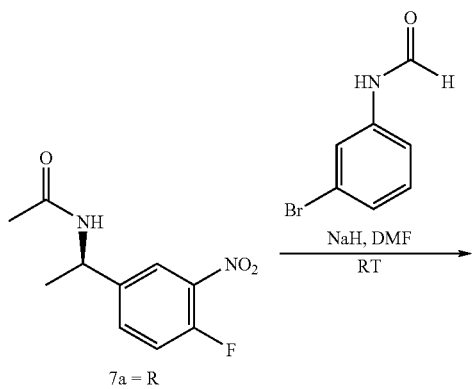

7a = R
7b = S

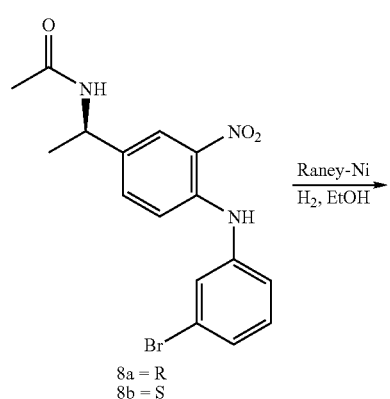

8a = R
8b = S

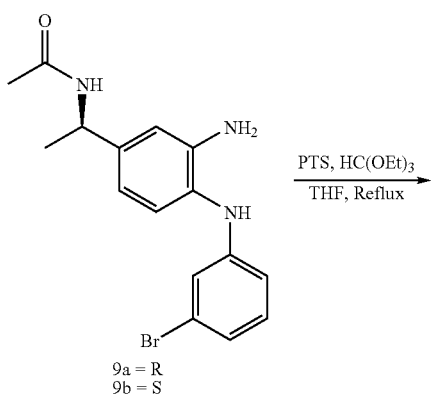

9a = R
9b = S

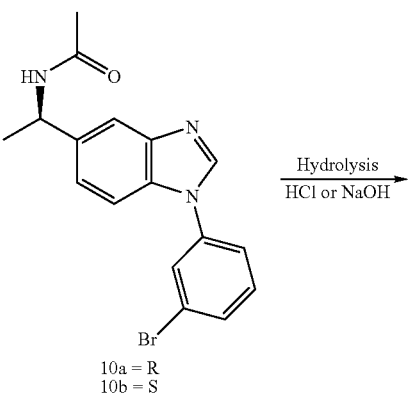

10a = R
10b = S

-continued

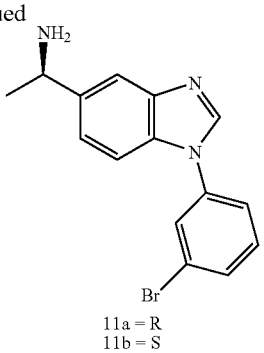

11a = R
11b = S

Synthesis of (R)-N-Acetyl-1-(4-fluorophenyl)-ethylamine (6a)

To a stirred solution of (R)-1-(4-fluorophenyl)-ethylamine 5a (24.6 g; 176 mmol) in toluene 100 ml was added drop wise Acetic anhydride (19.84 g; 194 mmol) while keeping the temperature under 40° C. using an ice bath. The reaction mixture was stirred overnight at RT. A white precipitate was formed and 300 ml Pet. Ether was added and the temperature adjusted to 5° C. The precipitate was filtered off and dried in the air. Yield 30 g; 94%. NMR and LCMS showed a pure material.

Synthesis of (R)-N-Acetyl-1-(4-fluoro3-nitrophenyl)-ethylamine (7a)

(S)-N-Acetyl-1-(4-fluorophenyl)-ethylamine 6a (29.5; 162 mmol) was dissolved in 80 ml concentrated Sulphuric acid, this gave a orange solution. This was then cooled to −15° C. and slowly added Nitric acid (7.5 ml; 179 mmol) dissolved in 30 ml $H_2SO_4$ conc. keeping the temperature below −15° C. After 1 h the reaction was finished as seen from TLC and the reaction mixture poured into ice. A sloppy precipitate formed and a small amount of $NH_4OH$ was added with the intension to basify the reaction mixture but suddenly a nice precipitate was formed and this was then collected and washed thoroughly with water. The precipitate was dissolved in EtOAc, dried with $MgSO_4$ and evaporated in vacuo to give 30.5 g; 83% yield of 7a. The compound was pure enough by NMR and LCMS for the next step.

Synthesis N-{(R)-1-[4-(3-Bromo-phenylamino)-3-nitrophenyl]-ethyl}-acetamide (8a)

N-formyl-3-bromoaniline (29 g; 145 mmol) was dissolved in 200 ml dry DMF and added NaH (6.36 g; 159 mmol) portionwise. When gas evolution ceased, (R)-N-Acetyl-1-(4-fluoro3-nitrophenyl)-ethylamine 7a (30 g; 132 mmol), dissolved in 100 ml DMF was added dropwise. After stirring for 48 h the reaction was finished and poured into ice/water and extracted with EtOAc (1 l). The organic phase was dried with MgSO4 and evaporated in vacuo. The product was an orange oil (57 g), which according to LCMS showed 49% product and 43% N-formylated product along with small impurities. The raw product was considered pure enough to proceed to the next step.

Synthesis of N-{(R)-1-[3-Amino-4-(3-bromo-phenylamino)-phenyl]-ethyl}-acetamide (9a)

N-{(R)-1-[4-(3-Bromo-phenylamino)-3-nitro-phenyl]-ethyl}-acetamide 8a (57 g) was dissolved in 400 ml EtOH and hydrogenated using Raney-Ni (200 mg) under a atmosphere of hydrogen. After hydrogen consumption ceased the reaction was worked up by filtering off the catalyst using Celite. The solvent was removed in vacuo and the yield was considered quantitative.

Synthesis of N-{(R)-1-[1-(3-Bromo-phenyl)-1H-benzoimidazol-5-yl]-ethyl}-acetamide (10a)

N-{(R)-1-[3-Amino-4-(3-bromo-phenylamino)-phenyl]-ethyl}-acetamide 9a ~50 g was dissolved in 200 ml dry THF and added anhydrous triethylorthoformate (51 g; 345 mmol) and p-toluenesulphonic acid (0.2 g). The reaction mixture was heated to reflux overnight. The reaction was worked up by evaporation of the THF followed by redissolvation in EtOAc. The organic phase was washed with diluted $NH_{4aq}$ and the organic phase was dried ($MgSO_4$) and evaporated in vacuo to give the crude product. This was then subjected to column chromatography using $DCM:MeOH:NH_{4aq}$ (97:3:0.1) as an eluent, to give 29.4 g, pure product.

Synthesis of (R)-1-[1-(3-Bromo-phenyl)-1H-benzoimidazol-5-yl]-ethylamine (11a)

N-{(R)-1-[1-(3-Bromo-phenyl)-1H-benzoimidazol-5-yl]-ethyl}-acetamide 10a (10 g, 26 mmol) was dissolved/suspended in 150 ml 6M HCl and heated to 80° C. for 4-5 days or until TLC showed no more starting material. The reaction mixture was cooled to RT and poured into 800 ml ice-cold 2M NaOH. The product was extracted with DCM and the organic phase dried ($MgSO_4$) and evaporated to give a brownish oil (8.8 g). This was then subjected to column chromatography using DCM:MeOH:NH4 aq (95:5:0.1) as an eluent, to give 7.3 g, pure product.

The corresponding S-enantiomers 6b-11b was obtained using the exact same experimental conditions for each individual steps as mentioned above.

General Procedure for Suzuki Coupling

To a solution of compound 10a, 10b, 11a or 11b (1 eq) and arylboronic acid or the corresponding arylboronic acid ester (1.1 eq) in mixture of solvents 1,2-dimethoxyethane and water (3:1) was added $Na_2CO_3$ (5 eq). The catalyst $(Ph_3P)_2PdCl_2$ (5 mol %) was added and the reaction mixture was stirred at 90° C. for 6-8 h.[The reaction was monitored by TLC]. The reaction mixture was cooled to RT, diluted with water, extracted with ethylacetate, dried over $Na_2SO_4$ and concentrated. The crude product was purified by silica gel column chromatography using ethylacetate in hexane as mobile phase to furnish biaryl compounds 12a-12aar. If the product was an oil it was redissolved in a minimum amount of THF and precipitated as a hydrochloride salt using 3M HCl in TBME.

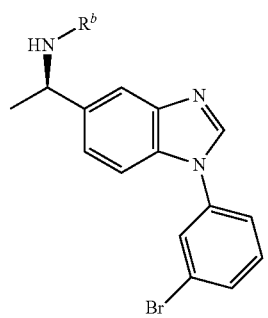

10a = R, $R^b$ = Ac
10b = S, $R^b$ = Ac
11a = R, $R^b$ = H
11b = S, $R^b$ = H

-continued

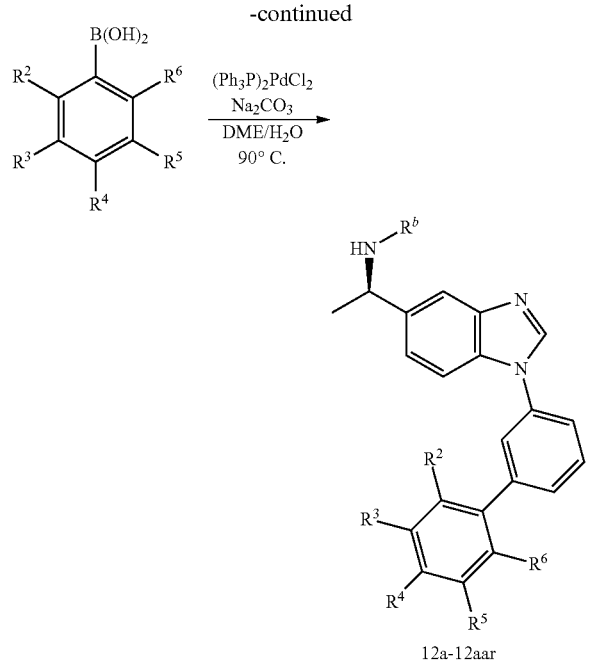

The following compounds were or can be prepared using the above mentioned protocol for Suzuki coupling:

| No. | Starting material | R/S | $R^b$ | $R^2$ | $R^3$ | $R^4$ | $R^5$ | $R^6$ |
|---|---|---|---|---|---|---|---|---|
| 12a | 10a | R | Ac | H | H | H | H | H |
| 12b | 10a | R | Ac | OMe | H | H | H | H |
| 12c | 10a | R | Ac | OMe | H | H | Cl | H |
| 12d | 10a | R | Ac | NHSO₂Me | H | H | H | H |
| 12e | 10a | R | Ac | CN | H | H | H | H |
| 12f | 10a | R | Ac | Ac | H | H | H | H |
| 12g | 10b | S | Ac | OMe | H | H | H | H |
| 12h | 10b | S | Ac | CN | H | H | H | H |
| 12i | 10b | S | Ac | H | H | H | H | H |
| 12j | 10b | S | Ac | OMe | H | H | Cl | H |
| 12k | 10b | S | Ac | NHSO₂Me | H | H | H | H |
| 12l | 10b | S | Ac | Ac | H | H | H | H |
| 12m1 | 10a | R | Ac | 4-methylbenzo[d][1,3]dioxol-yl | | | | |
| 12m2 | 10b | S | Ac | 4-methylbenzo[d][1,3]dioxol-yl | | | | |
| 12n | 11a | R | H | H | H | H | H | H |
| 12o | 11a | R | H | OMe | H | H | H | H |
| 12p | 11a | R | H | OMe | H | H | Cl | H |
| 12q | 11a | R | H | NHSO₂Me | H | H | H | H |
| 12r | 11a | R | H | CN | H | H | H | H |
| 12s | 11a | R | H | OMe | H | H | H | OMe |
| 12t | 11a | R | H | OMe | F | H | H | H |
| 12u | 11a | R | H | OMe | OMe | H | H | H |
| 12v | 11a | R | H | OMe | H | H | H | F |
| 12x | 11a | R | H | OMe | Cl | H | H | H |
| 12y | 11a | R | H | OMe | H | OMe | H | H |
| 12z | 11a | R | H | 4-methylbenzo[d][1,3]dioxol-yl | | | | |
| 12aa | 11a | R | H | OMe | H | H | F | F |
| 12ab | 11a | R | H | OMe | H | F | H | H |
| 12ac | 11a | R | H | Cl | H | H | CN | H |
| 12ad | 11a | R | H | OH | Cl | H | H | H |
| 12ae | 11a | R | H | F | Cl | H | H | F |
| 12af | 11a | R | H | CH₂-Morpholine | H | H | H | H |
| 12ag | 11a | R | H | OMe | F | H | F | H |
| 12ah | 11a | R | H | OMe | H | H | F | H |
| 12ai | 11a | R | H | OMe | H | H | H | Cl |
| 12aj | 11a | R | H | Cl | Me | H | H | F |
| 12ak | 11a | R | H | Cl | H | H | H | Cl |
| 12al | 11a | R | H | Piperazine | H | H | H | H |
| 12am | 11a | R | H | F | H | H | H | F |
| 12an | 11a | R | H | Cl | H | H | Me | F |
| 12ao | 11a | R | H | C(=O)NH₂ | H | H | H | H |
| 12ap | 11a | R | H | Ac | H | H | H | H |
| 12aq | 11a | R | H | OCF₃ | H | H | H | H |
| 12ar | 11b | S | H | H | H | H | H | H |
| 12as | 11b | S | H | OMe | H | H | H | H |
| 12at | 11b | S | H | C(=O)NH₂ | H | H | H | H |
| 12au | 11b | S | H | CN | H | H | H | H |
| 12av | 11b | S | H | Ac | H | H | H | H |
| 12ax | 11b | S | H | OCF₃ | H | H | H | H |
| 12ay | 11b | S | H | 4-methylbenzo[d][1,3]dioxol-yl | | | | |
| 12az | 11b | S | H | OMe | H | H | F | F |
| 12aaa | 11b | S | H | OMe | H | F | H | H |
| 12aab | 11b | S | H | Cl | H | H | CN | H |
| 12aac | 11b | S | H | OH | Cl | H | H | H |
| 12aad | 11b | S | H | F | Cl | H | H | F |
| 12aae | 11b | S | H | CH₂-Morpholine | H | H | H | H |
| 12aaf | 11b | S | H | OMe | F | H | F | H |
| 12aag | 11b | S | H | OMe | H | H | H | OMe |
| 12aah | 11b | S | H | OMe | F | H | H | H |
| 12aai | 11b | S | H | OMe | H | H | H | F |
| 12aaj | 11b | S | H | OMe | H | H | H | Cl |
| 12aak | 11b | S | H | Cl | Me | H | H | F |
| 12aal | 11b | S | H | OMe | H | OMe | H | H |
| 12aam | 11b | S | H | OMe | OMe | H | H | H |
| 12aan | 11b | S | H | Cl | H | H | H | Cl |
| 12aao | 11b | S | H | piperazine | H | H | H | H |
| 12aap | 11b | S | H | F | H | H | H | F |
| 12aaq | 11b | S | H | Cl | H | H | Me | F |
| 12aar | 11b | S | H | OMe | H | H | F | H |
| 12aas | 11a | R | H | CN | H | CF₃ | H | H |
| 12aat | 11b | S | H | CN | H | CF₃ | H | H |
| 12aau | 11a | R | H | CN | F | H | H | H |
| 12aav | 11b | S | H | CN | F | H | H | H |
| 12aaw | 10a | R | Ac | CN | H | F | H | H |
| 12aax | 10b | S | Ac | CN | H | F | H | H |
| 12aay | 11a | R | H | CN | H | F | H | H |
| 12aaz | 11b | S | H | CN | F | H | H | H |

N-[(R)-1-(1-Biphenyl-3-yl-1H-benzoimidazol-5-yl)-ethyl]-acetamide, Hydrochloride (12a)

LC-ESI-HRMS of [M+H]+ shows 356.1763 Da. Calc. 356.176287 Da, dev. 0 ppm

N-{(R)-1-[1-(2'-Methoxy-biphenyl-3-yl)-1H-benzoimidazol-5-yl]-ethyl}-acetamide (12b)

LC-ESI-HRMS of [M+H]+shows 386.1875 Da. Calc. 386.186852 Da, dev. 1.7 ppm

N-{(R)-1-[1-(5'-Chloro-2'-methoxy-biphenyl-3-yl)-1H-benzoimidazol-5-yl]-ethyl}-acetamide (12c)
LC-ESI-HRMS of [M+H]+shows 420.1474 Da. Calc. 420.14788 Da, dev. −1.1 ppm N-{(R)-1-[1-(2'-Methanesulfonylamino-biphenyl-3-yl)-1H-benzoimidazol-5-yl]-ethyl}-acetamide (12d)
LC-ESI-HRMS of [M+H]+ shows 449.1656 Da. Calc. 449.164737 Da, dev. 1.9 ppm N-{(R)-1-[1-(2'-Cyano-biphenyl-3-yl)-1H-benzoimidazol-5-yl]-ethyl}-acetamide (12e)
LC-ESI-HRMS of [M+H]+ shows 449.1656 Da. Calc. 449.164737 Da, dev. 1.9 ppm N-{(R)-1-[1-(2'-Acetyl-biphenyl-3-yl)-1H-benzoimidazol-5-yl]-ethyl}-acetamide (12f)
LC-ESI-HRMS of [M+H]+ shows 398.1874 Da. Calc. 398.186852 Da, dev. 1.4 ppm N-{(S)-1-[1-(2'-Methoxy-biphenyl-3-yl)-1H-benzoimidazol-5-yl]-ethyl}-acetamide (12 g)
LC-ESI-HRMS of [M+H]+ shows 386.186 Da. Calc. 386.186852 Da, dev. −2.2 ppm N-{(S)-1-[1-(2'-Cyano-biphenyl-3-yl)-1H-benzoimidazol-5-yl]-ethyl}-acetamide, Hydrochloride (12h)
LC-ESI-HRMS of [M+H]+ shows 381.1714 Da. Calc. 381.171536 Da, dev. −0.4 ppm N-[(S)-1-(1-Biphenyl-3-yl-1H-benzoimidazol-5-yl)-ethyl]-acetamide (12i)
LC-ESI-HRMS of [M+H]+ shows 356.1774 Da. Calc. 356.176287 Da, dev. 3.1 ppm N-{(S)-1-[1-(5'-Chloro-2'-methoxy-biphenyl-3-yl)-1H-benzoimidazol-5-yl]-ethyl}-acetamide, Hydrochloride (12j)
LC-ESI-HRMS of [M+H]+ shows 420.147 Da. Calc. 420.14788 Da, dev. −2.1 ppm N-{(S)-1-[1-(2'-Methanesulfonylamino-biphenyl-3-yl)-1H-benzoimidazol-5-yl]-ethyl}-acetamide, Hydrochloride (12k)
LC-ESI-HRMS of [M+H]+ shows 449.1649 Da. Calc. 449.164737 Da, dev. 0.4 ppm N-{(S)-1-[1-(2'-Acetyl-biphenyl-3-yl)-1H-benzoimidazol-5-yl]-ethyl}-acetamide, Hydrochloride (12l)
LC-ESI-HRMS of [M+H]+ shows 398.1864 Da. Calc. 398.186852 Da, dev. −1.1 ppm N-{(R)-1-[1-(3-Benzo[1,3]dioxol-4-yl-phenyl)-1H-benzoimidazol-5-yl]-ethyl}-acetamide (12m1)
LC-ESI-HRMS of [M+H]+ shows 400.1658 Da. Calc. 400.166117 Da, dev. −0.8 ppm N-{(S)-1-[1-(3-Benzo[1,3]dioxol-4-yl-phenyl)-1H-benzoimidazol-5-yl]-ethyl}-acetamide (12m2)
LC-ESI-HRMS of [M+H]+ shows 400.167 Da. Calc. 400.166117 Da, dev. 2.2 ppm (R)-1-(1-Biphenyl-3-yl-1H-benzoimidazol-5-yl)-ethylamine, Hydrochloride (12n)
LC-ESI-HRMS of [M+H]+ shows 314.1673 Da. Calc. 314.165722 Da, dev. 5 ppm (R)-1-[1-(2'-Methoxy-biphenyl-3-yl)-1H-benzoimidazol-5-yl]-ethylamine, Hydrochloride (12o)
LC-ESI-HRMS of [M+H]+ shows 344.1748 Da. Calc. 344.176287 Da, dev. −4.3 ppm (R)-1-[1-(5'-Chloro-2'-methoxy-biphenyl-3-yl)-1H-benzoimidazol-5-yl]-ethylamine, Hydrochloride (12p)
LC-ESI-HRMS of [M+H]+ shows 378.1383 Da. Calc. 378.137315 Da, dev. 2.6 ppm N-{3'-[5-((R)-1-Amino-ethyl)-benzoimidazol-1-yl]-biphenyl-2-yl}-methanesulfonamide (12q)
LC-ESI-HRMS of [M+H]+ shows 407.1563 Da. Calc. 407.154172 Da, dev. 5.2 ppm 3'-[5-((R)-1-Amino-ethyl)-benzoimidazol-1-yl]-biphenyl-2-carbonitrile (12r)
LC-ESI-HRMS of [M+H]+ shows 339.1604 Da. Calc. 339.160971 Da, dev. −1.7 ppm (R)-1-[1-(2',6'-Dimethoxy-biphenyl-3-yl)-1H-benzoimidazol-5-yl]-ethylamine, Hydrochloride (12s)
LC-ESI-HRMS of [M+H]+ shows 374.1863 Da. Calc. 374.186852 Da, dev. −1.5 ppm (R)-1-[1-(3'-Fluoro-2'-methoxy-biphenyl-3-yl)-1H-benzoimidazol-5-yl]-ethylamine, Hydrochloride (12t)
LC-ESI-HRMS of [M+H]+ shows 362.1684 Da. Calc. 362.166865 Da, dev. 4.2 ppm (R)-1-[1-(2',3'-Dimethoxy-biphenyl-3-yl)-1H-benzoimidazol-5-yl]-ethylamine, Hydrochloride (12u)
LC-ESI-HRMS of [M+H]+ shows 374.1873 Da. Calc. 374.186852 Da, dev. 1.2 ppm (R)-1-[1-(6'-Fluoro-2'-methoxy-biphenyl-3-yl)-1H-benzoimidazol-5-yl]-ethylamine, Hydrochloride (12v)
LC-ESI-HRMS of [M+H]+ shows 362.1686 Da. Calc. 362.166865 Da, dev. 4.8 ppm (R)-1-[1-(3'-Chloro-2'-methoxy-biphenyl-3-yl)-1H-benzoimidazol-5-yl]-ethylamine, Hydrochloride (12x)
LC-ESI-HRMS of [M+H]+ shows 378.1385 Da. Calc. 378.137315 Da, dev. 3.1 ppm (R)-1-[1-(2',4'-Dimethoxy-biphenyl-3-yl)-1H-benzoimidazol-5-yl]-ethylamine, Hydrochloride (12y)
LC-ESI-HRMS of [M+H]+ shows 374.1874 Da. Calc. 374.186852 Da, dev. 1.5 ppm (R)-1-[1-(3-Benzo[1,3]dioxol-4-yl-phenyl)-1H-benzoimidazol-5-yl]-ethylamine (12z)
LC-ESI-HRMS of [M+H]+ shows 358.1557 Da. Calc. 358.155552 Da, dev. 0.4 ppm (R)-1-[1-(2',3'-Difluoro-6'-methoxy-biphenyl-3-yl)-1H-benzoimidazol-5-yl]-ethylamine (12aa)

(R)-1-[1-(4'-Fluoro-2'-methoxy-biphenyl-3-yl)-1H-benzoimidazol-5-yl]-ethylamine (12ab)
LC-ESI-HRMS of [M+H]+ shows 362.1675 Da. Calc. 362.166865 Da, dev. 1.8 ppm 3'-[5-((R)-1-Amino-ethyl)-benzoimidazol-1-yl]-6-chloro-biphenyl-3-carbonitrile (12ac)

3'-[5-((R)-1-Amino-ethyl)-benzoimidazol-1-yl]-3-chloro-biphenyl-2-ol (12ad)

(R)-1-[1-(3'-Chloro-2',6'-difluoro-biphenyl-3-yl)-1H-benzoimidazol-5-yl]-ethylamine (12ae)

(R)-1-[1-(2'-Morpholin-4-ylmethyl-biphenyl-3-yl)-1H-benzoimidazol-5-yl]-ethylamine (12af)

(R)-1-[1-(3',5'-Difluoro-2'-methoxy-biphenyl-3-yl)-1H-benzoimidazol-5-yl]-ethylamine (12ag)
LC-ESI-HRMS of [M+H]+ shows 380.1578 Da. Calc. 380.157443 Da, dev. 0.9 ppm (R)-1-[1-(5'-Fluoro-2'-methoxy-biphenyl-3-yl)-1H-benzoimidazol-5-yl]-ethylamine (12ah)

(R)-1-[1-(6'-Chloro-2'-methoxy-biphenyl-3-yl)-1H-benzoimidazol-5-yl]-ethylamine (12ai)

(R)-1-[1-(2'-Chloro-6'-fluoro-3'-methyl-biphenyl-3-yl)-1H-benzoimidazol-5-yl]-ethylamine (12aj)

(R)-1-[1-(2',6'-Dichloro-biphenyl-3-yl)-1H-benzoimidazol-5-yl]-ethylamine (12ak)

(R)-1-[1-(2'-piperazin-1-yl-biphenyl-3-yl)-1H-benzoimidazol-5-yl]-ethylamine (12al)
The compound is synthesized via the N-Boc-piperazine intermediate which is then deprotected.

(R)-1-[1-(2',6'-Difluoro-biphenyl-3-yl)-1H-benzoimidazol-5-yl]-ethylamine (12am)

(R)-1-[1-(2'-Chloro-6'-fluoro-5'-methyl-biphenyl-3-yl)-1H-benzoimidazol-5-yl]-ethylamine (12an)

3'-[5-((R)-1-Amino-ethyl)-benzoimidazol-1-yl]-biphenyl-2-carboxylic acid amide (12ao)

1-{3'-[5-((R)-1-Amino-ethyl)-benzoimidazol-1-yl]-biphenyl-2-yl}-ethanone (12ap)

(R)-1-[1-(2'-Trifluoromethoxy-biphenyl-3-yl)-1H-benzoimidazol-5-yl]-ethylamine (12aq)

(S)-1-(1-Biphenyl-3-yl-1H-benzoimidazol-5-yl)-ethylamine, Hydrochloride (12ar)
LC-ESI-HRMS of [M+H]+ shows 314.1657 Da. Calc. 314.165722 Da, dev. −0.1 ppm (S)-1-[1-(2'-Methoxy-biphenyl-3-yl)-1H-benzoimidazol-5-yl]-ethylamine, Hydrochloride (12as)
LC-ESI-HRMS of [M+H]+ shows 344.1778 Da. Calc. 344.176287 Da, dev. 4.4 ppm 3'-[5-((S)-1-Amino-ethyl)-benzoimidazol-1-yl]-biphenyl-2-carboxylic acid amide (12 at)
LC-ESI-HRMS of [M+H]+ shows 357.1723 Da. Calc. 357.171536 Da, dev. 2.1 ppm 3'-[5-((S)-1-Amino-ethyl)-benzoimidazol-1-yl]-biphenyl-2-carbonitrile, Hydrochloride (12au)
LC-ESI-HRMS of [M+H]+ shows 339.1598 Da. Calc. 339.160971 Da, dev. −3.5 ppm 1-{3'-[5-((S)-1-Amino-ethyl)-benzoimidazol-1-yl]-biphenyl-2-yl}-ethanone, Hydrochloride (12av)
LC-ESI-HRMS of [M+H]+ shows 356.1768 Da. Calc. 356.176287 Da, dev. 1.4 ppm (S)-1-[1-(2'-Trifluoromethoxy-biphenyl-3-yl)-1H-benzoimidazol-5-yl]-ethylamine (12ax)
LC-ESI-HRMS of [M+H]+ shows 398.1495 Da. Calc. 398.148021 Da, dev. 3.7 ppm (S)-1-[1-(3-Benzo[1,3]dioxol-4-yl-phenyl)-1H-benzoimidazol-5-yl]-ethylamine, Hydrochloride (12ay)

(S)-1-[1-(2',3'-Difluoro-6'-methoxy-biphenyl-3-yl)-1H-benzoimidazol-5-yl]-ethylamine (12az)

(S)-1-[1-(4'-Fluoro-2'-methoxy-biphenyl-3-yl)-1H-benzoimidazol-5-yl]-ethylamine (12aaa)

3'-[5-((S)-1-Amino-ethyl)-benzoimidazol-1-yl]-6-chloro-biphenyl-3-carbonitrile (12aab)

3'-[5-((S)-1-Amino-ethyl)-benzoimidazol-1-yl]-3-chloro-biphenyl-2-ol (12aac)

(S)-1-[1-(3'-Chloro-2',6'-difluoro-biphenyl-3-yl)-1H-benzoimidazol-5-yl]-ethylamine (12aad)

(S)-1-[1-(2'-Morpholin-4-ylmethyl-biphenyl-3-yl)-1H-benzoimidazol-5-yl]-ethylamine (12aae)

(S)-1-[1-(3',5'-Difluoro-2'-methoxy-biphenyl-3-yl)-1H-benzoimidazol-5-yl]-ethylamine (12aaf)

(S)-1-[1-(2',6'-Dimethoxy-biphenyl-3-yl)-1H-benzoimidazol-5-yl]-ethylamine (12aag)

(S)-1-[1-(3'-Fluoro-2'-methoxy-biphenyl-3-yl)-1H-benzoimidazol-5-yl]-ethylamine (12aah)

(S)-1-[1-(6'-Fluoro-2'-methoxy-biphenyl-3-yl)-1H-benzoimidazol-5-yl]-ethylamine (12aai)

(S)-1-[1-(6'-Chloro-2'-methoxy-biphenyl-3-yl)-1H-benzoimidazol-5-yl]-ethylamine (12aaj)

(S)-1-[1-(2'-Chloro-6'-fluoro-3'-methyl-biphenyl-3-yl)-1H-benzoimidazol-5-yl]-ethylamine (12aak)

(S)-1-[1-(2',4'-Dimethoxy-biphenyl-3-yl)-1H-benzoimidazol-5-yl]-ethylamine (12aal)

(S)-1-[1-(2',3'-Dimethoxy-biphenyl-3-yl)-1H-benzoimidazol-5-yl]-ethylamine (12-aam)

(S)-1-[1-(2',6'-Dichloro-biphenyl-3-yl)-1H-benzoimidazol-5-yl]-ethylamine (12aan)

(S)-1-[1-(2'-piperazin-1-yl-biphenyl-3-yl)-1H-benzoimidazol-5-yl]-ethylamine (12ao)
The compound is synthesized via the N-Boc-piperazine intermediate which is then deprotected.

(S)-1-[1-(2',6'-Difluoro-biphenyl-3-yl)-1H-benzoimidazol-5-yl]-ethylamine (12aap)

(S)-1-[1-(2'-Chloro-6'-fluoro-5'-methyl-biphenyl-3-yl)-1H-benzoimidazol-5-yl]-ethylamine (12aaq)

(S)-1-[1-(5'-Fluoro-2'-methoxy-biphenyl-3-yl)-1H-benzoimidazol-5-yl]-ethylamine (12aar)

3'-[5-((R)-1-Amino-ethyl)-benzoimidazol-1-yl]-4-trifluoromethyl-biphenyl-2-carbonitrile (12aas)

3'-[5-((S)-1-Amino-ethyl)-benzoimidazol-1-yl]-4-trifluoromethyl-biphenyl-2-carbonitrile (12aat)

3'-[5-((R)-1-Amino-ethyl)-benzoimidazol-1-yl]-3-fluoro-biphenyl-2-carbonitrile (12aau)

3'-[5-((S)-1-Amino-ethyl)-benzoimidazol-1-yl]-3-fluoro-biphenyl-2-carbonitrile (12aav)

N-{(R)-1-[1-(2'-Cyano-4'-fluoro-biphenyl-3-yl)-1H-benzoimidazol-5-yl]-ethyl}-acetamide (12aaw)

N-{(S)-1-[1-(2'-Cyano-4'-fluoro-biphenyl-3-yl)-1H-benzoimidazol-5-yl]-ethyl}-acetamide (12aax)

3'-[5-((R)-1-Amino-ethyl)-benzoimidazol-1-yl]4-fluoro-biphenyl-2-carbonitrile (12aay)

3'-[5-((S)-1-Amino-ethyl)-benzoimidazol-1-yl]-4-fluoro-biphenyl-2-carbonitrile (12aaz)

Test Methods

Test Method 1

In Vitro Inhibition of $^3$H-flunitrazepam ($^3$H-FNM) Binding

The GABA recognition site and the benzodiazepine modulatory unit can selectively be labelled with $^3$H-flunitrazepam.

Tissue Preparation

Preparations are performed at 0-4° C. unless otherwise indicated. Cerebral cortex from male Wistar rats (150-200 g) is homogenised for 5-10 sec in 20 ml Tris-HCl (30 mM, pH 7.4) using an Ultra-Turrax homogeniser. The suspension is centrifuged at 27,000×g for 15 min and the pellet is washed three times with buffer (centrifuged at 27,000×g for 10 min). The washed pellet is homogenized in 20 ml of buffer and incubated on a water bath (37° C.) for 30 min to remove endogenous GABA and then centrifuged for 10 min at 27,000×g. The pellet is then homogenized in buffer and centrifuged for 10 min at 27,000×g. The final pellet is resuspended in 30 ml buffer and the preparation is frozen and stored at −20° C.

Assay

The membrane preparation is thawed and centrifuged at 2° C. for 10 min at 27,000×g. The pellet is washed twice with 20 ml 50 mM Tris-citrate, pH 7.1 using an Ultra-Turrax homogeniser and centrifuged for 10 min at 27,000×g. The final pellet is resuspended in 50 mM Tris-citrate, pH 7.1 (500 ml buffer per g of original tissue), and then used for binding assays. Aliquots of 0.5 ml tissue are added to 25 µl of test solution and 25 µl of $^3$H-FNM (1 nM, final concentration), mixed and incubated for 40 min at 2° C. Non-specific binding is determined using Clonazepam (1 µM, final concentration). After incubation the samples are added 5 ml of ice-cold buffer and poured directly onto Whatman GF/C glass fibre filters under suction and immediately washed with 5 ml ice-cold buffer. The amount of radioactivity on the filters is determined by conventional liquid scintillation counting. Specific binding is total binding minus non-specific binding.

Results 25-75% inhibition of specific binding must be obtained, before calculation of an $IC_{50}$.

The test value will be given as $IC_{50}$ (the concentration (µM) of the test substance which inhibits the specific binding of $^3$H-FNM by 50%).

$$IC_{50} = (\text{applied test substance concentration, } \mu M) \times \frac{1}{\left(\frac{C_o}{C_x} - 1\right)}$$

where
$C_o$ is specific binding in control assays, and
$C_x$ is the specific binding in the test assay.
(The calculations assume normal mass-action kinetics).
Test results from these experiments with a number of compounds of the invention are shown in Table 1 below.

TABLE 1

| Test compound | In vitro binding IC$_{50}$ (μM) |
|---|---|
| Compound 3a | 0.073 |
| Compound 12o | 0.0067 |
| Compound 12b | 0.060 |
| Compound 12g | 0.0026 |
| Compound 12r | 0.0037 |

The invention claimed is:

1. A compound selected from the group consisting of 3'-[5-((R)-1-Amino-ethyl)-benzoimidazol-1-yl]-biphenyl-2-carbonitrile; an N-oxide of 3'-[5-((R)-1-amino-ethyl)-benzoimidazol-1-yl]-biphenyl-2-carbonitrile; and a pharmaceutically acceptable salt of 3'-[5-((R)-1-amino-ethyl)-benzoimidazol-1-yl]-biphenyl-2-carbonitrile.

2. A pharmaceutical composition comprising
   (a) 3'-[5-((R)-1-amino-ethyl)-benzoimidazol-1-yl]-biphenyl-2-carbonitrile, an N-oxide of 3'-[5-((R)-1-amino-ethyl)-benzoimidazol-1-yl]-biphenyl-2-carbonitrile, or a pharmaceutically acceptable salt of 3'-[5-((R)-1-amino-ethyl)-benzoimidazol-1-yl]-biphenyl-2-carbonitrile; and
   (b) at least one of a pharmaceutically acceptable carrier, a pharmaceutically acceptable excipient and a pharmaceutically acceptable diluent.

3. The compound of claim 1, wherein the compound is a pharmaceutically acceptable salt selected from the group consisting of hydro-chloride salts, hydrobromide salts, nitrates, perchlorates, phosphates, sulphates, formates, acetates, aconates, ascorbates, benzenesulphonates, benzoates, cinnamates, citrates, embonates, enantates, fumarates, glutamates, glycolates, lactates, maleates, malonates, mandelates, methanesulphonates, naphthalene-2-sulphonates, phthalates, salicylates, sorbates, stearates, succinates, tartrates, and toluene-p-sulphonates.

4. The compound of claim 1, wherein the compound is a pharmaceutically acceptable salt selected from the group consisting of sodium salts, potassium salts, calcium salts, magnesium salts, zinc salts, aluminum salts, lithium salts, choline salts, lysinium salts, and ammonium salts.

5. The compound of claim 1, wherein the compound is a pharmaceutically acceptable salt selected from the group consisting of alkyl-onium salts, cycloalkyl-onium salts, and cycloalkylalkyl-onium salts.

6. The pharmaceutical composition of claim 2, comprising about 0.1 mg to about 1000 mg of 3'-[5-((R)-1-amino-ethyl)-benzoimidazol-1-yl]-biphenyl-2-carbonitrile, the N-oxide of 3'-[5-((R)-1-amino-ethyl)-benzoimidazol-1-yl]-biphenyl-2-carbonitrile, or the pharmaceutically acceptable salt of 3'-[5-((R)-1-amino-ethyl)-benzoimidazol-1-yl]-biphenyl-2-carbonitrile.

7. The pharmaceutical composition of claim 2, comprising about 10 mg to about 500 mg of 3'-[5-((R)-1-amino-ethyl)-benzoimidazol-1-yl]-biphenyl-2-carbonitrile, the N-oxide of 3'-[5-((R)-1-amino-ethyl)-benzoimidazol-1-yl]-biphenyl-2-carbonitrile, or the pharmaceutically acceptable salt of 3'-[5-((R)-1-amino-ethyl)-benzoimidazol-1-yl]-biphenyl-2-carbonitrile.

8. The pharmaceutical composition of claim 2, comprising about 30 mg to about 100 mg of 3'-[5-((R)-1-amino-ethyl)-benzoimidazol-1-yl]-biphenyl-2-carbonitrile, the N-oxide of 3'-[5-((R)-1-amino-ethyl)-benzoimidazol-1-yl]-biphenyl-2-carbonitrile, or the pharmaceutically acceptable salt of 3'-[5-((R)-1-amino-ethyl)-benzoimidazol-1-yl]-biphenyl-2-carbonitrile.

* * * * *